(12) United States Patent
Aspelund et al.

(10) Patent No.: US 6,655,221 B1
(45) Date of Patent: Dec. 2, 2003

(54) MEASURING MULTIPHASE FLOW IN A PIPE

(75) Inventors: Audun Aspelund, Nesttun (NO); Tor Wideröe, Houston, TX (US)

(73) Assignee: Flowsys AS, Bergen (NO)

( * ) Notice: Subject to any disclaimer, the term of this patent is extended or adjusted under 35 U.S.C. 154(b) by 0 days.

(21) Appl. No.: 09/869,994

(22) PCT Filed: Jan. 10, 2000

(86) PCT No.: PCT/NO00/00005

§ 371 (c)(1),
(2), (4) Date: Oct. 4, 2001

(87) PCT Pub. No.: WO00/45133

PCT Pub. Date: Aug. 3, 2000

(30) Foreign Application Priority Data

Jan. 11, 1999 (NO) .......................................... 19990111

(51) Int. Cl.$^7$ ................................................ G01F 1/74
(52) U.S. Cl. .................................................. 73/861.04
(58) Field of Search ....................... 73/861.02, 861.04, 73/861.63, 861.42, 861.66, 61.44, 64.44, 1.34, 861.06; 324/693; 702/100

(56) References Cited

U.S. PATENT DOCUMENTS

| | | | | |
|---|---|---|---|---|
| 4,829,831 A | * | 5/1989 | Kefer et al. ............. | 73/861.02 |
| 4,834,051 A | * | 5/1989 | Tanaka et al. ............. | 123/703 |
| 4,974,452 A | * | 12/1990 | Hunt et al. ................. | 137/896 |
| 5,367,911 A | | 11/1994 | Jewell et al. | |
| 5,461,930 A | | 10/1995 | Farchi et al. | |
| 5,485,743 A | * | 1/1996 | Taherian et al. ............. | 73/61.44 |
| 5,591,922 A | * | 1/1997 | Segeral et al. ............. | 73/861.04 |
| 6,272,915 B1 | * | 8/2001 | Kostelnicek et al. ...... | 73/152.28 |
| 6,426,615 B1 | * | 7/2002 | Mehta ........................ | 324/71.4 |

FOREIGN PATENT DOCUMENTS

| | | |
|---|---|---|
| EP | 0510774 | 10/1992 |
| GB | 2313445 | 11/1997 |
| GB | 2330660 | 1/1999 |

* cited by examiner

Primary Examiner—Hezron Williams
Assistant Examiner—Jewel V. Thompson
(74) Attorney, Agent, or Firm—Ladas & Parry

(57) ABSTRACT

The method and the measuring system in accordance with the invention utilizes a measurement of electrical fields to determine the electrical characteristics of phases in a multiphase mixture constituting a fluid flow through a conduit. This is used as part of the determination of the phase fractions. Further, one uses time-varying signals from at least one pair of detectors for the electrical characteristics of the fluid, combined with the use of a cross-correlation for determining one or several velocities in the flowing fluid. Additionally, one or several pressure drops are measured across, or adjacent to, a narrow passage. By combining measurements of the electrical characteristics, with measurements of pressure drop, the fractions of all phases in the flow are determined. Combined with measurements of the velocities, the volume flow rates are calculated for the phases and by further combining this with the mass densities of the phases, the mass flow rates of the phases are determined.

18 Claims, 6 Drawing Sheets

MEASURING MULTIPHASE FLOW IN A PIPE

FIELD OF THE INVENTION

The invention relates to a method and a system for flow measurement of a two-phase liquid/liquid or liquid/gas mixture, or a three-phase liquid/liquid/gas mixture flowing through a production or transport pipe. The method and the system shall be used for measuring the percentage composition of phases in the pipe cross section at any time, as well as the individual phase velocities. Hence, from these measurements, the method and the system provide opportunities for calculating the volumetric flow rate of each respective phase in the two-phase or three-phase mixture. Additionally, knowing the mass densities of the individual phases, it is also possible to calculate the mass flow rates of the phases. The method and the system are in particular directed to applications within oil and gas production industry, where phases in a two-phase mixture may typically be hydrocarbons in liquid form, like crude oil or condensate, and hydrocarbons in gas form—natural gas, or crude oil/condensate and produced or injected water. The phases in a three-phase mixture may typically be crude oil/condensate, water and natural gas.

BACKGROUND OF THE INVENTION

During production of oil and gas, it is desirable to carry out flow measurement, in the form of mass flow rate or volume flow rate, of a pipe flow consisting of a two-phase or three-phase combination of oil/water/gas, so called multiphase measurement, This can be done using permanently installed measurement systems, e.g. on a marine production platform or on a land-based production plant. Such measurement systems are little by little replacing conventional measurement methods comprising bulky test separators complete with single-phase flow meters like turbine meters and measurement orifices measuring individual phases after separation thereof. It is important to measure the quantity produced from a reservoir to be able to control and regulate the production process in an effective manner. This enables optimum total production over the lifetime of a field, it is also desirable to measure the production from single wells individually, since a change in one individual well, for instance a sudden increase in the water production, is difficult to detect by measuring the collective production from several wells. Often, fiscal elements are also involved, wherein it is an important point to allocate the production from individual wells to the rightful owners, where the production from such wells is processed in a common processing plant with a different owner structure than the wells. It would also be desirable to be able to measure produced oil with an accuracy that is sufficient for buying and selling, but so far this is not realistic when using multiphase meters.

Many of the recent oil finds are located in small reservoirs at relatively large water depths, and in such cases it is often not possible to defend conventional development solutions, like for instance today's marine production platforms. In order to extract these marginal resources, large efforts have therefore been made to develop underwater systems. These systems comprise both wellhead control, manifold systems and, gradually, separators, and one can see contours of complete processing plants located on the sea floor. In this connection, a need has also come up for measuring the production flow down at the sea floor, and therefore, multiphase meters are about to be installed for such applications.

It has also become of interest to be able to measure flow rates continuously downhole, and development work is presently going on regarding such instrumentation. Today's well measurements are often carried out on a temporary basis, for instance as production logging where measurement systems are introduced down into the well by means of wireline or coil piping. This is expensive, and provides to a large degree qualitative measurements. Relatively long time may also pass between execution of such measurements, so that there is a risk of regulating the wells in accordance with old data, even if the production may have changed in the meantime. Besides, lately the complexity of the oil wells has increased strongly, due to new and more advanced methods within drilling and completion technology, and production from layered reservoirs, multibranch and horizontal wells have become ordinary practice, Being able to execute continuous downhole multiphase measurement on a permanent basis, will enable effective reservoir control, and in combination with e.g. valves for controlling influx from the reservoir, it is possible to achieve so-called "intelligent wells" that will result in increased oil extraction, reduced water production and eventually reduced intervention frequency. Today permanent well instrumentation consists substantially of pressure and temperature gauges, and to some degree Venturi meters for liquid rate measurements. To a certain degree, flow models are utilized that are based on measurements from pressure and temperature gauges located in different places, conservation laws for mass and moment, thermodynamic relations, physical parameters and reference measurements from logging. However, these methods depend on the "goodness" of the models, i.e. the ability to predict the individual flow rates of phases within the necessary uncertainties, and on correct assumptions regarding the physical and geometrical parameters in the well. They also require a high degree of calibrating in situ to obtain the desired precision.

When oil, water and gas flow simultaneously through a pipe, the distribution of the three phases may form a large number of different regimes or patterns, both axially and radially. Therefore, the influence of the flow on a measuring system will vary correspondingly, which becomes apparent particularly when measurements are carried out continuously over time. Generally, the flow will consist of a continuous and a discontinuous phase. Ordinarily, the liquid is the continuous phase, with free gas as the discontinuous phase. The free gas may be distributed substantially in two ways, like larger pockets, or like myriads of very small bubbles atomized in the liquid phase. In addition, some gas will often be dissolved in the oil phase, particularly under high pressures. As regards the liquid per se, it may be continuous oil with water drops distributed in the oil. This occurs often early in the lifetime of a well, when the oil usually is the dominating phase as to percentage. Moreover, this mixture is electrically insulating. In the opposite case with continuous water flow, oil drops are distributed in the water, which provides an electrically conductive liquid phase. The size of the distributed drops may vary, and the mixing mechanisms may be different, all the way from stable emulsions to more loose mixtures of the two phases. Essentially the liquid will be transported as one phase with one common velocity. Exceptions herefrom are in low flow velocities, where oil and water can be subject to complete or part separation, and when the pipe has an inclination deviating from the horizontal plane. In this case, gravity will make the heaviest component, usually the water, move with lower velocity than the oil. This difference in velocity is often termed "slip". In a well flow it may also happen that the water has a negative velocity relative to the general flow direction. As the well pressure decreases, more free gas will be produced, and it may happen that the gas becomes the dominating flow phase. Then the liquid will often be distributed as a film flowing relatively slowly along the pipe wall, in combination with a drop phase that to a larger degree accompanies the gas. Since the mass density of the gas is usually substantially lower than the mass density of the liquid phase, there will, as a rule, always exist slip between gas and liquid. The situations described above are often divided into main groups with designations bubble flow, slug flow, chum flow, layered flow and annular flow. A measurement system should therefore be able to make measurements under all of the above described flow situations, including cases with velocity slip between phases, and in particular between liquid and gas

SUMMARY OF THE INVENTION

In the following, the present invention is described in the form of a system for measuring characteristic parameters of a multiphase flow of crude oil or condensate, produced and/or injected water, and natural gas in a transport pipe, as well as a method that uses the measured parameters for determining the individual flow rates for crude oil/condensate, water and natural gas. The system comprises a compact sensor body having a substantially circular cross section, which sensor body is located centrally inside a transport pipe having a relatively constant inner diameter and having a circular cross section. The sensor body will in a first variant form a coaxial sensor wherein the flow is transported in an annular space between the body exterior and the inner pipe surface. In another variant, the sensor insert will be designed as a sensor insert shaped in principle inverted in relation to the first one, with a diameter choke having a transition from a diameter equal to the inner diameter of the transport pipe, through a reduction of the diameter to a cylindrical part and thereafter an increase of the diameter again to an inner diameter equal to the transport pipe inner diameter.

Further, the sensor body is placed concentrically in relation to the transport pipe. When the multiphase fluid flows through the pipe, a differential pressure will arise between an area upstream of the sensor insert and the area midway on the sensor insert, due to the cross section area narrowing caused by the insert. Thus, the system is provided with a first differential pressure meter to measure said differential pressure continuously over time. This differential pressure will depend on the total mass flow rate, and thereby it will also indirectly depend on the mass density of the multiphase fluid. The sensor insert itself is provided with several electrodes having in part different sizes, for measuring the electrical characteristics of the fluid moving in the narrowing mentioned above, by measuring the electrical field between the individual electrodes mentioned above and counter electrode means thereto. The system contains electronic circuitry suitable for the task, having inputs and outputs for this purpose. The method consists in using the measurement of the electrical field, together with a second measurement, for calculating the phase fractions, while the quick, time-varying values of the electrical field from a first pair of electrodes are cross-correlated to determine the velocity of the gas phase in the flow. Per se known physical models are utilized for the measurement principles mentioned above, and these models are combined to convert the measured values of the differential pressure and electrical characteristics, to phase fractions of oil, water and gas. All calculations are made in a calculation unit suitable therefor, in the form of a computer provided with inputs to accept all relevant signals from the individual gauges/meters, a program calculating and storing the desired quantities, as well as outputs for outputting the result of the calculations. By introducing further differential pressure gauges, there are essentially four ways in which to utilize the device for determining fractions and volume flow rates. These ways will be described in a more detailed manner below.

In a first embodiment of the method, the electrical signals from a second pair of electrodes on the sensor body are cross-correlated in order to find the liquid phase velocity. This velocity can be expressed as a function of the measured differential pressure, the mass densities of the individual phases, presumed to be known, the gas fraction and the water-in-liquid fraction. The measured electrical quantity can also be expressed as a function of the gas fraction and the water-in-liquid fraction, as well as the electrical characteristics of the individual phases, also presumed to be known. By solving these equations, the three phase fractions will be found. Since the velocities of the liquid and gas phases are also measured, the volume flow rates of the individual phases can be determined by multiplying individual phase fractions by the respective flow rates and the cross section area. Further, it will be possible to determine the mass flow rates of the individual phases by multiplying the volume flow rates by the respective mass densities of the individual phases.

In a second embodiment, a second differential pressure gauges can be mounted in a position in the downstream end of the sensor body, at the transition from the body and back to the open pipe. There a differential pressure will arise between a position in the annular space and a position downstream of the body. This differential pressure signal will in principle be a mirror-inverted version of the first differential pressure, and may, by first being inverted, be cross-correlated with the first differential pressure, and provide the liquid velocity in a corresponding manner as when cross-correlating the electrical signals. Thereby, the cross-correlation of the electrical signals can be substituted, and further, phase fractions and volume flow rates can be calculated in a similar manner as described above regarding the first embodiment of the method.

In a third embodiment of the method, a third differential pressure gauge can be used at a certain distance upstream or downstream in relation to the sensor body. By means of this third differential pressure gauge, a differential pressure can to be measured that is dependent on the mass density of the three-phase mixture, due to the static pressure difference arising because of the weight of the mixture. This presumes that the pipe is placed approximately vertically, so that the two terminals of the third differential pressure gauge are mounted with a certain minimum vertical distance. Since the mass density of the mixture is a function of the mass densities of the individual phases, and the three phase fractions, it is possible, by combining this with the measurement on the electrical field between one of the electrodes and the pipe wall, to calculate the three phase fractions. In this case the first differential pressure measurement will be used to determine the liquid flow rate, using the momentum equation, while the second differential pressure measurement becomes redundant. In all these three embodiments of the method, the coaxial variant of the sensor body will be used, and further one will use cross-correlation of the electrical signals from the first electrode pair to determine the gas velocity, which velocity is in most cases supposed to be different from the liquid velocity.

In a fourth embodiment of the method in accordance with the invention, the principle is substantially identical to the third embodiment, but the sensor insert is constituted by a sensor Insert providing a choking of the pipe with a central passage for the flow. In this case, the electrical sensor units are constituted by pairs of electrode/counter electrode devices placed inside the cylindrical part of the narrowing, since it is no longer possible to use the transport pipe wall as a counter electrode. Moreover, the first and the third differential pressure gauge will be used like in the third embodiment, and the gas velocity will be measured by cross-correlation between a pair of the above mentioned electrode devices.

DESCRIPTION OF THE PRIOR ART

It is previously known from Norwegian patent application no. 971791 (Japan National Oil Corp., Yokogawa Electric Corp., NKK Corp., Japan Petroleum Exploration Co. Ltd., Teikoku Oil Co. Ltd.) a device that utilizes principles that may to some degree exhibit similarity with the present invention. The common features are that both inventions measure velocity and phase fractions in a multiphase mixture, and both utilize one or several coaxial sensors measuring the electrical characteristics in the three-phase mixture flowing between an outer electrode shaped as a cylinder and an inner, cylindrical electrode, placed concentrically inside the pipe. Further, cross-correlation is made between two sensors placed a fixed distance apart along the pipe axis, in order to determine one or several velocities. Finally, the electrical measurement principle can be combined with a pressure drop gauge to determine one of the fractions by combining the pressure drop equation with the equation for the electrical characteristics. However, the two inventions exhibit substantial difference in that the instrument described in patent application no. 971791 measures the dielectric constant between two outer, separate excitation electrodes respectively, which electrodes are excited by a sweep of frequencies through the microwave range, and a concentrically placed, inner common electrode, possibly two separate such electrodes, lying constantly on the electrical ground potential. The inner electrode is hollow, ie. tubular, so that the flow passes both on the inside and the outside thereof. In the present invention, the electrical field is measured between several electrodes on the outside of a massive, substantially cylindrical, inner body placed concentrically inside the pipe, and associated counter electrodes. In patent application no. 971791, measurements are made by varying the frequency through a relatively large range, and thereafter two frequencies are selected in order to measure one individual phase fraction in the liquid. First, the water fraction is measured by measuring the permittivity difference at the two frequencies, based on the dielectric loss of the water, or dispersion, in this range. Thereafter, the oil fraction is measured in a similar manner, at two other frequencies, provided that the oil has a dielectric loss in the swept frequency range. If the oil is without loss, one uses a measurement from a flow meter of the differential pressure type with the momentum equation valid therefor, combined with one of the impedance measurements, for determining the oil fraction. The differential pressure gauge is placed upstream of the impedance sensors, and separate therefrom. The gas fraction is always calculated by subtracting the two other phase fractions from the sum of fractions that is equal to 1. The embodiment of the present invention that reminds of the flow meter described in patent application no. 971791, differs therefrom in that it first measures the velocity of the complete liquid phase by cross-correlation between two measurements of the electrical characteristics. At the same time, a pressure drop is measured between a position e.g. upstream in relation to the inner body and a position in the narrowing along said body. The general momentum equation for pressure drop gauges, in which the liquid velocity is included, is then combined with the equation for the electrical characteristics, in order to determine the gas fraction as well as the water-in-liquid fraction at the same time. Another important difference is that in the present invention, one and the same body is utilized both for generating a pressure drop and for measuring the electrical characteristics, so that both measurements are made in approximately one and the same position. In addition, the gas velocity is measured by means of a second cross-correlation between a second pair of electrodes on the inner body. In patent application no. 971791 there is no description regarding a separate measurement of the gas velocity, only of water and oil. In the case where the instrument described in patent application no. 971791 uses the momentum equation to determine the oil fraction, it is presumed that there is no velocity difference between phases after having these phases mixed in a static mixer upstream of the gauges.

Another invention that has some features in common with the present invention, is described in U.S. Pat. No. 4,829,831. The features common to the present invention are that it utilizes a differential pressure device with a second sensor unit within the throat of the throttling device. This gives two, but only two independent measurements, enabling it to measure one mass flow rate and two cross-section fractions. The last option is based on the physical necessity that the two phase fractions always sum up to 1, and can be determined if the two fluids have different physical properties in relation to the operation principle of the inherent sensor unit. It is also emphasized that the positioning of the inherent sensor unit, being it a capacitance or density sensor, within the narrowing of the throttling device gives an increased accuracy of the measurement, due to the claimed homogenizing effect on the fluid by the throttling device.

The present invention has several features separating it substantially from the technology disclosed in U.S. Pat. No. 4,829,834. While the US patent describes a system that is able to measure two fractions and one flow rate, the present invention can handle three phase fractions and two different velocities. It is admitted that the positioning of the capacitance device within the narrowing of the throttling device has a positive effect on the accuracy when measuring on a two-phase liquid-liquid mixture, due to a certain homogenizing effect. However, when handling a two-phase liquid-gas fluid, this homogenizing effect is limited as far as the radial mixing is concerned, and even less as regards longitudinal mixing. This means that e.g. in the frequently occurring intermittent flow with large gas pockets separated by liquid slugs, and normally with a velocity difference between the gas and liquid phase, the effect of a throttling device is very limited concerning equalizing the velocities. Experiments have shown that this is independent of whether the device is installed horizontally or vertically.

The positioning of the electric measurement devices within the narrowing of the present invention, has basically nothing to do with the possible exploitation of any homogenizing effect. The reasons are rather the gain in performing all the measurements at the same time and in the same place, in addition to the benefit of achieving a compact and simple design of the unit.

U.S. Pat. No. 5,367,911 describes a device with some features in common with the present invention. This is a device for measuring the velocity of a multi-phase flow in an annulus between a centrally placed tool and the inside of a pipe wall, using sensors responding to some characteristics of the flow. More specifically, the invention describes sensors for qualitative detection of conductivity/resistivity, or sensors using acoustic signals to detect such characteristics. At least two sensors are mutually displaced along the flow direction for enabling the use of cross-correlation for determination of velocity. A possibility of combining different electrodes in case of a multi-electrode unit, is also indicated, in order to vary the sensitivity with and the separation of the sensors, but there is not specific information about how this is used. Further, there is no indication of doing any quantitative measurement to achieve information about the phase cross-section fractions, and the publication does not mention means for measuring permittivity when the fluid is nonconducting. Neither is there any indication of the ability to measure the different velocities of the gas and liquid phases in the cases of slip between the liquid and gas. A final feature separating it from the present invention, is that it does not contain any means for detecting the flow rates (mass or volume) by using any differential pressure, or similar device. Basically, this US patent describes a velocity meter for a flowing fluid containing some detectable discontinuity.

European patent application no. EP-A2-0510774 describes a method and to an apparatus with some features common to the present invention. These include the use of multiple capacitance sensors to measure permittivity of a fluid, two cross-correlations to measure the liquid and gas flow velocities, and determination of flow rates by combination of these measurements. The capacitance sensors of the European publication use a common excitation electrode and multiple detector electrodes, and detector electrodes can be selected to fulfil the inventors purposes. In contrast, the present invention uses autonomous electrode pairs where each capacitance or conductance is measured between each pair. Measurement of cross-section fractions in EP-A2-0510774 is basically done by one measurement combined with the physical entity given in equation 3 of the present application. This gives two equations with three unknowns, and is insufficient to determine the three fractions. It is therefore argued that the liquid mixture contains no gas near the bottom of the pipe, such that the water cut of the liquid phase can be determined. However, those skilled in the art of multiphase measurement have experienced that liquid slugs contain gas bubbles (see also page 5, lines 24–25in the European publication), and is a three phase medium that requires two independent measurements. The system described in EP-A2-0510774 does not measure the conductivity in cases where the fluid is conductive, i.e. at water cuts larger than 40%. The system detects that the fluid is conductive, but gives no quantitative measurement of the conductivity. This appears in FIG. 5 of EP-A2-510774, where the capacitance does change as a function of the permittivity, exemplified by pure gas (E), pure oil (F) and oil with some water content (G). In water continuous flow the indicated capacitance value is lower than the measurement for gas, which is actually a result of a short-circuited capacitance meter (H), and is independent of the oil content of the water. In contrast, the present invention also measures the conductivity of the fluid quantitatively, in a similar way as the permittivity measurement. It is pointed out by the inventor of EP-A2-0510774 that his invention operates advantageously in intermittent flow regimes, and that almost all applications flow in this regime. However, it must be emphasized that many applications exhibit other regimes, e.g. very well mixed flow with tiny gas bubbles distributed in the liquid. The present invention is designed to handle all types of regimes, and therefore does not suffer from such indicated limitations. Finally, the system of EP-A2-0510774 does not contain a differential pressure device, and thereby not to the possibilities for combinations of measurements to solve the necessary equations, in the way the present invention does.

Further, from Norwegian patent no. 304333 (Fluenta AS) there is previously known a method and a means for measuring fractions in a multiphase flow. The features common with the present invention are that one uses measurement of the electrical characteristics for determining the electrical characteristics of the three-phase mixture flooring through an opening between two electrodes. In both cases this is combined with another measuring principle that is sensitive regarding the mass density of the mixture. The equations from the two measurement principles are coupled in order to calculate the three component fractions. However, the method and the instrument described in patent no. 304333 differ substantially, since in that case a gamma densitometer is specified, which densitometer contains a radioactive source and a gamma detector, constituting the other measuring principle, while the present invention utilizes a variant of one or several pressure drop gauges when calculating the fractions in particular, there is a substantial difference where the present invention in based on first measuring the liquid velocity by means of cross-correlation, like in the first and the second embodiment of the device, and thereafter calculating the phase fractions from the combination of the two other measurements. Also the third and fourth embodiment of the present invention are substantially different, where the mass density of the present invention is provided by measuring differential pressure, and not by gamma densitometry. Moreover, the sensor design is quite different, since patent no. 304333 specifies a nonintrusive sensor having opposite electrodes incorporated into the pipe wall, however separated from the flowing medium by an insulating material. The present invention uses an intrusive sensor having several cylindrical electrodes in contact with the flow, where the electrical field is measured between these electrodes and the pipe wall, possibly directly between two electrodes placed in the narrowing.

Moreover, a measuring principle is also previously known from U.S. Pat. No. 5,693,891 (Brown, A., Allen, J.) for measuring the quantity of a two-phase mixture flowing through a pipe. This is a measuring device that uses a pipe narrowing with a smooth transition from a larger to a smaller diameter, and differential pressure measurement thereover for calculating the flow rate of two-phase liquid/liquid or liquid/gas. In addition a second differential pressure is measured over two points along the pipe with different height level, in order to determine the mass density (gradiomanometer principle) of the fluid. Then, the density is used for calculating the flow rate, in order to obtain the total rate. In other respects, this is the same principle as described in U.S. Pat. No. 4,856,344, except that the two patents use somewhat different combinations of positions along the pipe for measuring differential pressure. In both of the two patented measuring systems mentioned above, three pressure tap points placed in succession along the pipe are used, the central point being common to the two differential pressure measurements. The common feature with the present invention, is measuring the differential pressure between a point upstream of a narrowing and a point within the narrowing, and using the relation between differential pressure and flow rate to calculate a desired parameter. Generally, this is well know technology from the Venturi principle. The most important dissimilarities are that the inventions described in U.S. Pat. Nos. 5,693,891 and 4,856, 344 both lack electrical measuring principles and hence can only be used for measuring a two-phase mixture. In the present invention, both in the first and in the second embodiment, first a velocity is measured that is used in the relation between volume flow rate and differential pressure. Thereafter, this relation is combined with the relation between the electrical characteristics of the phases and the fraction ratio, and the equation system is solved with regard to all three phase fractions. In the third and fourth embodiment of the present invention, the differential pressure for flow rate measurement is provided by a narrowing that also contains electrodes for determining the electrical characteristics of the fluid, and the material of the narrowing also has a function as an electrical insulator between the electrodes and the surroundings. Thus, this constitutes a separate, combined sensor insert to be incorporated in an ordinary transport pipe. In addition, the present invention uses two pairs of pressure tap points, i.e. four altogether, that are independent of each other, for measuring the two differential pressures.

A combination of one of the two last mentioned publications, U.S. Pat. No. 5,693,891 or U.S. Pat. No. 4,856,344, and Norwegian patent no. 304333, would possibly provide a complete multiphase flow meter by utilizing the flow rate resulting from U.S. Pat. No. 5,693,891 or 4,856,344, and calculating the phase fractions from the device described in patent no. 304333, and thereafter calculating the phase flow rates, provided that all phases flow with the same velocity. In the present invention, the gamma densitometer has been made redundant. Since the flow velocity can be measured by cross-correlation between two measurements of electrical fields, like in the first embodiment of the device, the present invention will hence constitute a further improvement of an envisaged combination of the above publications, since there is a possibility for using only one differential pressure gauge. In addition, the present invention will comprise one additional velocity measurement to determine the gas velocity when it is different from the liquid velocity. Such a device has not been described in any of the above three patents, and these patents therefore cannot handle velocity slip between the phases. However, the most important difference is that none of the above mentioned patents describes a combination of an electrical measurement and a differential pressure measurement in one and the same unit, so that these measurements can be carried out in one and the same position, or within a very limited area around the same position.

OBJECTS OF THE INVENTION

The method and the system in accordance with the invention are defined precisely in the appended patent claims.

The method and the system underlying the present invention, are based on robust principles having a long history of good results within the field of flow measuring. By using a system in accordance with this invention, the following advantages will be achieved.

The invention does not contain any radioactive sources, which means that one avoids the dangers, and not a least the rules prevailing regarding transporting, storing, using and returning radioactive material. Additionally, the system is independent of possible coatings of radioactive material, which is something that may be found often in production piping for crude oil.

Electromagnetic principles make it possible with a simple and sturdy construction, and the use of relatively low-frequency electronics, is already qualified for underwater and downhole applications. In addition, the use of qualified and robust, physical models will provide reliability for the system.

Differential pressure gauges are reliable, and have been used by many operators within the field of multiphase measurement for a long time. The dynamic range of such gauges is wide, and it can be used for 0–100% gas fraction.

It is possible to make a very compact instrument, resulting in low weight and little need of space in comparison with other instruments in the market.

Standard piping can be used, only with taps for differential pressure measurements, absolute pressure measurement and temperature measurement, which gives substantial savings in relation to the special constructions used in many existing systems.

Figure 1:
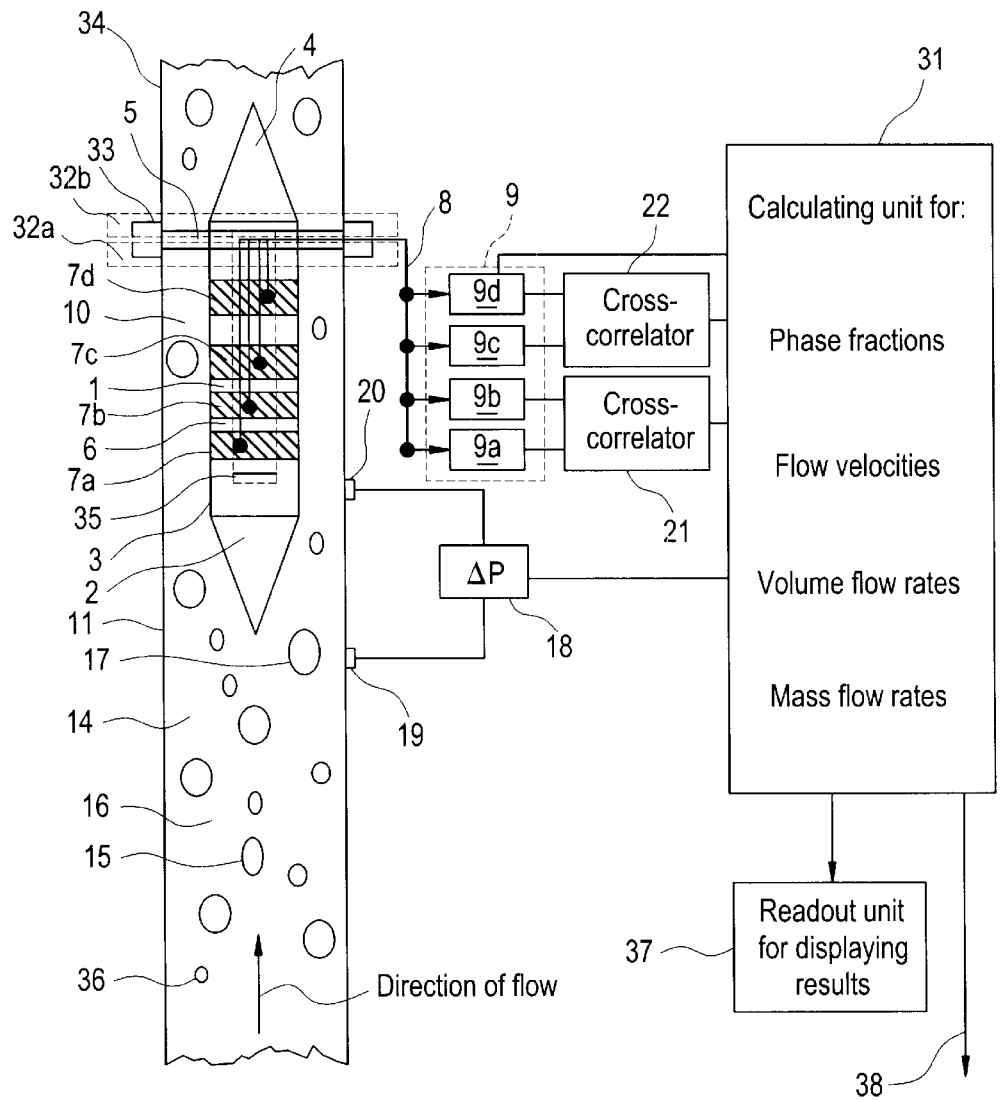
FIG. 1 shows a first embodiment of the invention, with the transport pipe, the sensor body with electrodes, as well as a differential pressure gauge in the upstream end of the sensor body.

It is now referred to FIG. 1, in which the first embodiment of the invention is illustrated. The inner sensor body 1 of the device has a circular cross section with a varying diameter in the axial direction of pipe 11. It has an entrance section 2 with an increasing diameter in the flow direction, which is vertically upward in accordance with the arrow in FIG. 1, and continues in a cylindrical measurement section 3 and ends in an exit section 4 having a decreasing diameter so as to form a streamlined body 1. The entrance and exit sections 2, 4 have a gradual, smooth change of diameter (e.g. conical) respectively before and after the transition to the measurement section 3. This ensures that the permanent pressure drop over sensor body 1 will be as small as possible, since the sensor body 1 construction creates the smallest possible turbulence and friction. The above mentioned transition sections 2 and 4 can equally well have a curved (e.g. parabolic) change of diameter. Further, the entrance and exit sections 2, 4 will be made from an erosion resistant material in order to resist possible influence from particles in the fluid flow 14. This material may be a high quality metal, an industrial ceramic or another material having the property of high resistance toward mechanical wear. The sensor body 1 is supported in stays 5 attached in a ring 33 having the same inner diameter as the transport pipe, and which is attached between two flanges 32a and 32b, one flange 32a belonging to the pipe 11 in which the sensor body 1 has been mounted, and the other flange 32b belonging to an adjacent pipe 34 mounted downstream in relation to the above mentioned pipe 11. These stays 5 may be mounted slanted or at right angles in relation to the longitudinal axis of the pipe, and at the same time they will, one or several of them being hollow, work as lead-throughs for wires 8 between the sensor body 1 and the electronics unit 9 on the outside of pipe 11.

The cylindrical part of the sensor body 1, also termed the measuring section 3, consists alternately in the longitudinal direction of cylindrical elements 6 made from an electrically insulating material, and cylindrical, metallic electrodes 7a–d, in such a manner that they form a smooth unit. The insulating elements 6 may be made from a thermoplastic or some other suitable electrically insulating material. Further, the elements must have an inner diameter 35 as small as possible to ensure strength for the body, however with sufficiently large diameter 35 to make room for wires 8 from the electrodes 7a–d to the electronics unit 9. Correspondingly, the metallic electrodes 7a–d will also have external shape as cylinders with an inside hole that corresponds to the inner diameter 35 of the insulating modules 6. Thus, the wires 8 will be passed from the inside of the measuring section 3, through the stays 5 and to the outside of the flow pipe 11. There, the wires are guided further to an electronics unit 9 on the outside of pipe 11 via wire lead-throughs in the flange ring 33.

Figure 2:
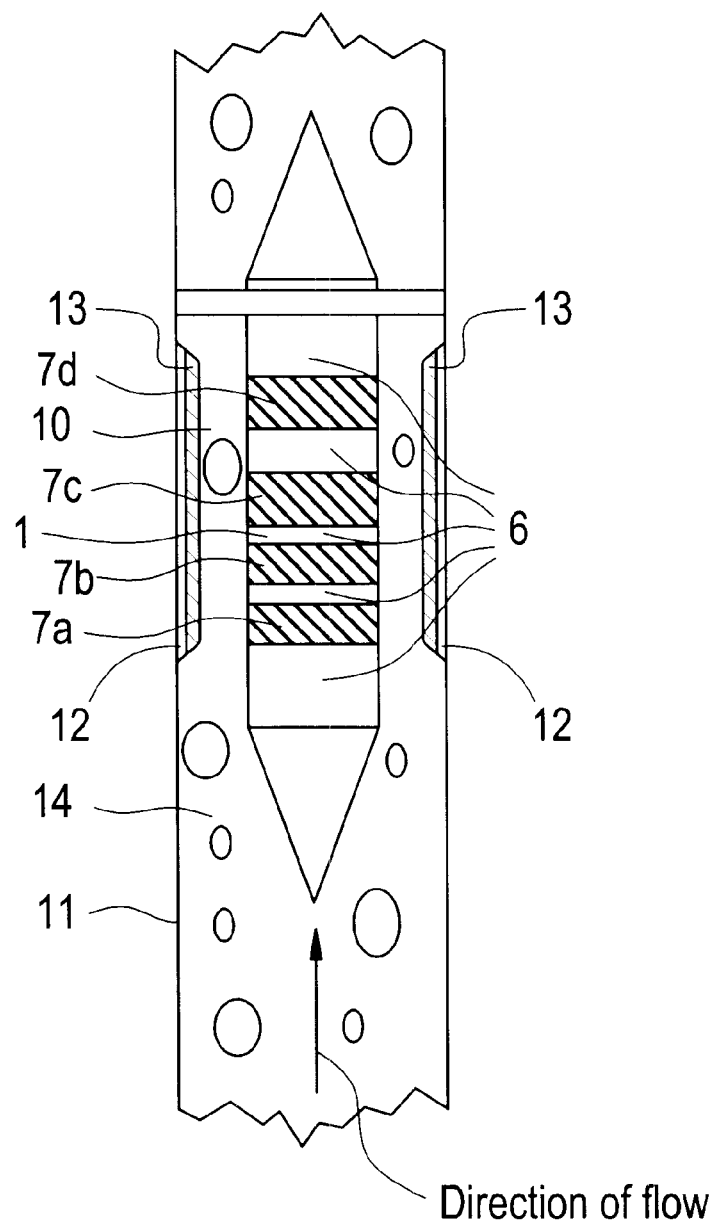
FIG. 2 shows a detail of a variant of the invention with the transport pipe, the sensor body including electrodes, the stays as well as an outer excitation electrode.

This sensor design results in a coaxial sensor that is characterized by two particular advantages; it is one of the most sensitive types of sensor for measuring electrical characteristics, and it provides a symmetrical geometry in the measuring area 10 in the annular space between the measuring section 3 and the pipe 11, rendering the electrical field a symmetrical field. The electrodes 7a–d may have different length, and the distance between them may vary, depending on what they are intended to measure. Substantially there will be two pairs of measurement electrodes 7a and 7b as well as 7c and 7d, where one pair 7a and 7b consists of equally large, but relatively short electrodes with a relatively short distance therebetween. The second pair 7c and 7d consists of equally large, but somewhat longer electrodes with a relatively large distance therebetween. In addition, the measuring section 3 can be provided with further electrodes as required, so called "guard electrodes", to ensure that the electrical field in the measuring area 10 is as homogenous as possible. The guard electrodes will in such cases be driven on the same electrical potential as the measurement electrodes 7a–d, and geometrically they will be placed closely adjacent the measurement electrodes 7a–d The method consists in continuously measuring the electrical field between electrodes 7a–d and the wall of pipe 11 in the measuring area 10 so as to determine the electrical characteristics of the, fluid 14 flowing at any moment in the annular space 10 between measuring section 3 and the inside of flow pipe 11. This can be done in two ways. One way is to excite the electrodes 7a–d on the sensor body 1 with an electrical voltage, and measure the magnitude of the electrical field between these electrodes 7a–d and the wall of pipe 11, which is held on electrical ground potential. In this case is will be particularly important to use guard electrodes. The second way is illustrated in FIG. 2, and is executed by placing a large cylindrical electrode 12 out next to the wall of pipe 11 in such a manner that it is placed concentrically with pipe 11, but insulated therefrom by means of an electrically insulating material 13. Such an electrode will have a length that is at least the size of the distance from the upstream end of the first electrode 7a, to the downstream end of the last electrode 7d on sensor body 1. Using this principle, the above mentioned cylindrical electrode 12 is excited with an electrical voltage, and one measures the magnitude of the electrical field between this electrode 12 and the individual electrodes 7a–d on sensor body 1 which in this case electrically may be on a virtual ground potential. The electrical characteristics of the flowing medium 14 depend on the fraction ratio (e.g. a percentage) between oil, water and gas in the fluid flow 14, and, again referring to FIG. 1, output signals representing this fraction ratio are obtained from the electronic circuits 9a–d. Several physical models exist regarding the interrelation between fraction ratios and electrical characteristics for a mixture of fluids 14. As an example, it can be referred to the Boyle model for parallel-oriented spheroids of a phase 15 distributed in a continuum of another phase 16. In this model, the electrical characteristics are expressed through the permittivities (the dielectric constants) of the individual phases in a mixture, as well as the permittivity of the mixture 14 itself, as a function of the fraction of the discontinuous phase 15 in the mixture 14. For a two-phase liquid/liquid mixture 14 wherein the discontinuous phase 15 is water drops distributed in a continuum 16 of oil, the following exemplary model may be usable:

$$\frac{\varepsilon_{watt} - \varepsilon_{liq}}{\varepsilon_{watt} - \varepsilon_{oil}} \cdot \left(\frac{\varepsilon_{oil}}{\varepsilon_{liq}}\right)^{A_2} = 1 - \phi_{wat}/(\phi_{wat} + \phi_{oil})$$

$$= 1 - \phi_{wat}$$

Equation 1.

with only oil and water present, because $\phi_{wat} + \phi_{oil} = 1$, and wherein $\epsilon_{wat}$, $\epsilon_{oil}$ and $\epsilon_{liq}$ are the permittivities of water, oil and liquid mixture respectively, fast is the water fraction in the liquid phase, and $A_a$ is a form factor depending on the shape of the spheroids. For perfect small balls, this form factor is typically ⅓. The relative sum of the water fraction and the oil fraction is in this case equal to 1, which gives the second necessary equation for this system. It is then possible to calculate the fractions of the two phases 15 and 16 directly, since the permittivities of the individual phases are presumed to be known, while the permittivity of the liquid mixture is a result of the measured quantity.

The model above can also be generalized for use in a three phase mixture where the liquid is regarded as a well mixed, continuous phase 16, with gas bubbles as a discontinuous phase 15 distributed in a corresponding manner as above:

$$\frac{\varepsilon_{gas} - \varepsilon_{mix}}{\varepsilon_{gas} - \varepsilon_{liq}} \cdot \left(\frac{\varepsilon_{liq}}{\varepsilon_{max}}\right)^{A_2} =$$

$$1 - \phi_{gas}/(\phi_{wat} + \phi_{oil} + \phi_{gas}) = 1 - \phi_{gas}$$

Equation 2.

with both oil, water and gas present (because $\phi_{wat} + \phi_{oil} + \phi_{gas} = 1$), and wherein $\epsilon_{gas}$ and $\epsilon_{mix}$ are the permittivities of the gas and the three-phase mixture, respectively, and $\phi_{gas}$ is the gas fraction. In the equation above, $\epsilon_{mix}$ is the result of the measured quantity, and it appears that this quantity is given as an implicit parameter. The permittivities of the individual phases are presumed to be known beforehand. $\epsilon_{liq}$ can be eliminated by combining Equation 2 and Equation 1. For the rest, in this case it is the relative sum of the water fraction, the oil fraction and the gas fraction that is equal to 1, given by the general relation:

$$\phi_{gas} + \phi_{wat} + \phi_{oil} = 1$$

Equation 3.

Thereby, one has two equations, but one further equation is needed to find the fractions for all three phases. This problem will be reverted to, after first having looked at further use of the measurements of the electrical characteristics. As far as it goes, Equation 1 and Equation 2 may be substituted by other models regarding the relation between the same parameters, or by models regarding the relation between e.g. the conductivities of the individual phases and the fraction ratios. Thus, in the last mentioned case, the conductivity will represent the measured electrical characteristics.

By measuring the electrical field in the measuring area 10 continuously over time, and simultaneously sampling individual measurements using a relatively high frequency, one will receive time-varying signals from detectors 9a–d expressing more or less random variations in the fraction ratios in the fluid 14 in the corresponding time period. This time variation illustrates the flow dynamics which is due to the many possible flow patterns. If such a pattern stays reasonably constant in the short time span when passing an electrode pair 7a and 7b or 7c and 7d, the signals will repeat themselves from one electrode, e.g. 7a, to the other, e.g. 7b. These signals can therefore be used to calculate one of the velocities in the flow by means of the per se known method of cross-correlation, where the cross-correlation coefficient, $R_{xy}(t)$, is calculated using the following formula:

$$R_{xy}(\tau) = \lim_{T \to \infty} \frac{1}{T} \int_0^T x(t-\tau) \cdot y(t) dt \qquad \text{Equation 4.}$$

By cross-correlating signals x(t) and y(t), one finds the time delay t from the moment when a disturbance 17 in the fluid flow 14 passes e.g. the first large electrode 7c (upstream), to the moment when it passes the second large electrode 7d (downstream), through the fact that the cross-correlation coefficient will assume its maximum value there. Since the distance between electrodes is known, it is a simple matter to calculate the velocity of the disturbance 17. In practice, this is carried out by sending the respective signals from the detector circuits 9c, providing signal x(t), and 9d, providing y(t), and that are connected to their respective electrodes 7c and 7d, into a cross-correlator 22. Such a cross-correlator 22 may be either a commercially available microelectronics circuit handling the signals from the detector circuits 9c and id directly, or part of the software in a calculating unit 31 handling data after initial processing thereof in an input stage. It is often so that relatively large electrodes like e.g. 7c and 7d, tend to detect large variations 17 in the flow, e.g. due to large gas bubbles, while they will be likely to filter out small variations 36 that would be due to small inhomogenities in the liquid phase. From this reason, the measured velocity will represent substantially the velocity of large gas bubbles, $v_{gas}$. On the contrary, the small electrodes 7a and 7b have a length that is shorter than the large electrodes 7c and 7d, and therefore they have an ability for spatial resolution that is more acute. Hence, these electrodes can detect small variations 36 in the flow. The small variations 36 are caused by correspondingly small gas bubbles and/or small water drops or accumulations of such water drops distributed in the oil. These small disturbances 36 will normally have a transport velocity that is approximately equal to the average liquid velocity, $v_{liq}$. As far as it goes, the signals from the small electrodes 7a and 7b may also contain information about the larger disturbances in the flow 14, and hence they can also be used for measurement of the velocity of these larger disturbances. In the same manner as with the signals from detector circuits 9c and 9d for the large electrodes 7c and 7d, the time-varying signals from detectors 9a and 9b for the small electrodes 7a and 7b, give signals x(t) and y(t) for processing in a cross-correlator 21, thereby to determine a velocity that is representative for the velocity of the liquid, $v_{liq}$.

DETAILED DESCRIPTION OF THE PREFERRED EMBODIMENTS

In the calculations referred to above, one further equation is necessary to determine the fractions, and in this invention a differential pressure measurement is used to solve this problem. The sensor body 1 will namely cause a pressure drop, $\Delta P$, when the flow passes through the narrowed area 10 in the annular space between the sensor body 1 and the pipe wall 11. This differential pressure is measured by means of a suitable differential pressure gauge 18, between a position 19 upstream in relation to the sensor body 1, and a position 20 along the cylindrical part 3 of the sensor body 1, in the measuring section. Of course, this differential pressure can be measured in a similar manner also between a position at the cylindrical part of the sensor body 1, and a position downstream from the same sensor body 1. By means of per se known, physical relations, one can use the differential pressure for determining the total mass flow rate, Q, in the pipe. Such a general physical relation is given in Equation 5 below:

$$Q = \epsilon E C_D A_2^M \sqrt{2 \cdot \rho \cdot \Delta P} \qquad \text{Equation 5}$$

wherein:

$$E = \frac{1}{\sqrt{1-\beta^4}}$$

$$\varepsilon = f\left(\frac{\Delta P}{P}, \gamma, \beta\right)$$

$$\beta = \sqrt{1 - \frac{d^2}{D^2}}$$

$$A_2^M = \frac{\pi}{4}(D^2 - d^2)$$

$C_D$ is the "discharge coefficient"

$\gamma$ is "specific heat ratio"

$\rho$ is the mass density of fluid 14

$\Delta P$ is the measured differential pressure from gauge 18 d is the outer diameter of sensor body 1

D is the inner diameter of pipe 11

Q is, as mentioned, the total mass flow rate in the pipe, and we have the following general and well-known relations $Q = q_{oil}\rho_{oil} + q_{wat}\rho_{wat} + q_{gas}\rho_{gas} = q_{liq}\rho_{liq} + q_{gas}\rho_{gas}$.

q representing volume flow rates of the respective phases.

It has been shown (eg. in Hammer, E. A., Nordtvedt, J. E.: "Scientific/Technical Report No. 239: MULTIPHASE FLOW MEASUREMENT USING A VENTURIMETER", University of Bergen, November 1990) that in connection with a liquid/gas flow, one may use the following expression for the volume flow rate of the liquid phase, assuming low pressure so that gas mass density can be disregarded:

$$q_{liq} = \varepsilon E C_D A_2^M \sqrt{\frac{2(1-\phi_{gas})\Delta P}{\rho_{liq}}} \qquad \text{Equation 6.}$$

By utilizing the obvious relation in Equation 7:

$$q_{liq} = v_{liq}\phi_{liq}\text{Å} = v_{liq}(1-\phi_{gas})\text{Å} \qquad \text{Equation 7.}$$

and combine this with Equation 6 hereabove, the result is:

$$1-\phi_{gas} = \frac{2(\varepsilon E C_D A_2^M)^2 \Delta P}{\rho_{liq} v_{liq}^2 A^2} \qquad \text{Equation 8.}$$

From Equation 8 one can see that the gas fraction, $\phi_{gas}$, is directly dependent upon the mass density of the mixture, $\rho_{liq}$, the liquid velocity, $v_{liq}$, and the pipe cross section area, A, as well as the measured differential pressure, $\Delta P$. There exists also a known relation for the mass density of the fluid, where the mass densities of the individual phases are presumed known:

$$\rho_{mix} = \phi_{gas}\rho_{gas} + \phi_{oil}\rho_{oil} + \phi_{wat}\rho_{wat} \approx \phi_{oil}\rho_{oil} + \phi_{wat}\rho_{wat} = \rho_{liq}\cdot(1-\phi_{gas}), \qquad \text{Equation 9.}$$

while in general the following holds true:

$$\rho_{liq} = \frac{\phi_{wat}}{\phi_{wat}+\phi_{oil}}\cdot\rho_{wat} + \frac{\phi_{oil}}{\phi_{wat}+\phi_{oil}}\cdot\rho_{oil}$$

For relatively low pressures, the gas density will be negligible in relation to the densities of the liquids, and the density of the mixture will be approximately the same as the liquid density, as appears from Equation 9 hereabove. At higher pressures, this is not necessarily the case, and then this must be taken into consideration, and the equations must be amended correspondingly.

In the first embodiment of the present invention, the velocity of the liquid is measured by means of cross-correlation of the electrical signals from detectors 9a and 9b, by means of the cross-correlator 21 as referred to above, and the gas fraction is included in the permittivity model given in Equation 2. By substituting for $\rho_{liq}$ in Equation 8, one obtains a second equation, where $\phi_{gas}$ is expressed by means of the two other phase fractions, and together with Equation 2 and Equation 3, it is hence possible to solve with regard to all three phase fractions. It is here presumed that the mass densities of the individual phases are known, so that Equation 9 can be used in the calculations Since the velocity of the liquid has already been measured, the oil and water flow rates are found by multiplying the measured velocity by the phase fractions of oil and water respectively, and by the pipe cross section area. As previously described, also the velocity of the gas will be measured, by means of a cross-correlation of signals from detectors 9c and 9d coupled to the two electrodes 7c and 7d in the measuring section 3 of sensor body 1. This is done in cross-correlator 22 Thereby one finds also in a simple manner the flow rate of the gas, in a similar manner as described regarding the liquid phases hereabove. If the mass flow rates are desirable, these can be obtained by multiplying the volume flow rates of the individual phases by their respective mass densities. This invention has the obvious advantage that one is independent of other types of density gauges, for example gamma densitometers containing radioactive sources. Another advantage is that the differential pressure gauge 18 is very fast in relation to a gamma densitometer, and therefore it is able to follow the flow variations at the same rate as the electrical field measuring device 9, and hence ensure that representative data are measured at any time. In addition, measurements are also carried out in the same physical position, so as to obtain a complete synchronization of the measurement.

Figure 3:
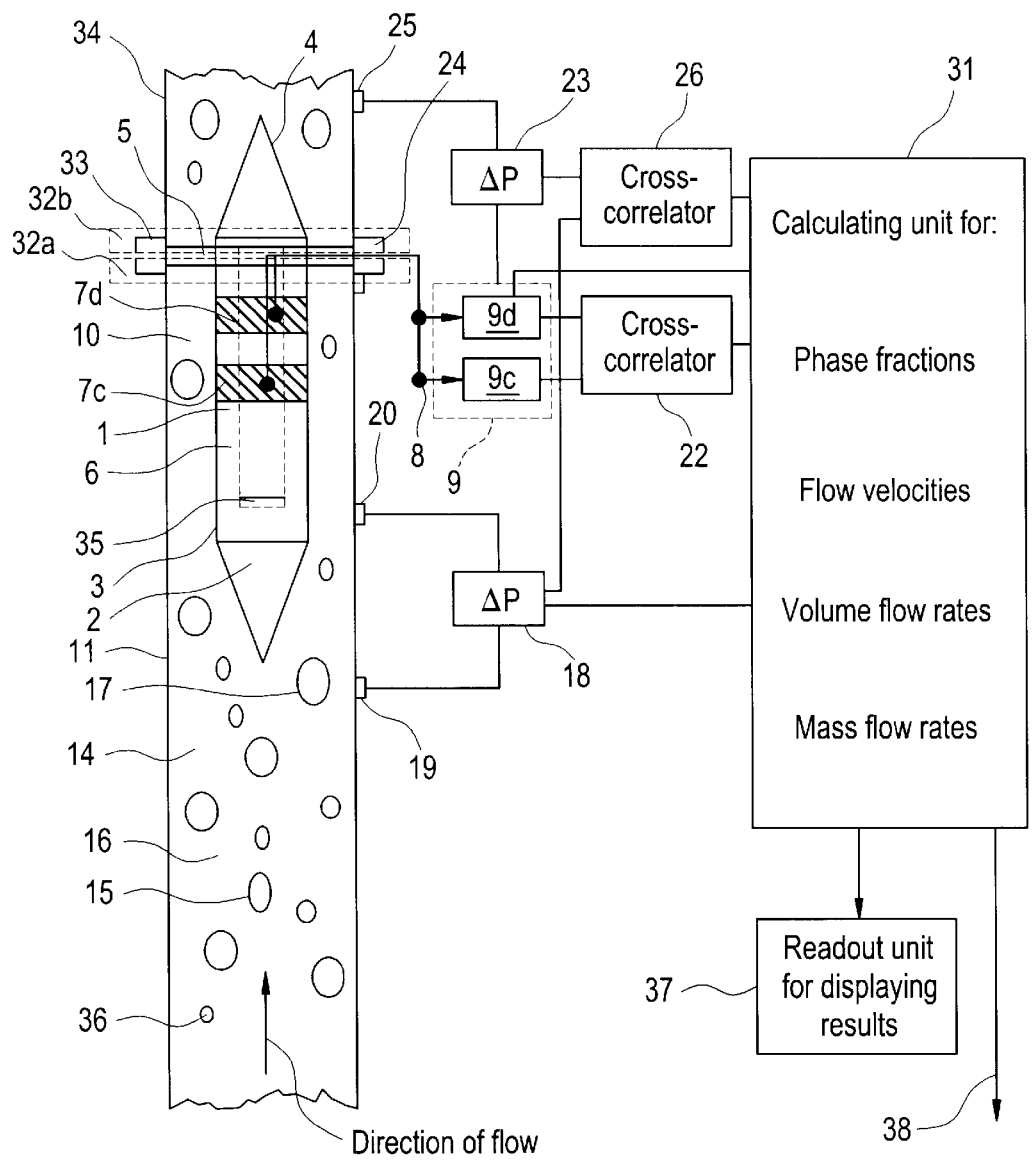
FIG. 3 shows a second embodiment of the invention with the transport pipe, the sensor body including electrodes, a differential pressure gauge in the upstream end of the sensor body and a differential pressure gauge in the downstream end of the sensor body.

In another embodiment of the invention, referring to FIG. 3 and presuming that the first differential pressure gauge has been mounted in the upstream end of sensor body 1, a second differential pressure gauge 23 is introduced for measuring the pressure difference between a point 24 in the measuring area 10 and a measuring point 25 downstream from sensor body 1. The distance from point 24 in the annular space to the measuring point 25 downstream from sensor body 1, is ideally the same as the distance from measuring point 19 upstream from sensor body 1 to the measuring point 20 in the narrowed area 10 in the measuring section 3 measured by the first differential pressure gauge 18. Thereby, the two measured differential pressures will be approximately similar in magnitude. If the time variation in the signals from the differential pressure gauges 18 and 23 are considered, they will be approximately uniform in the two cases, except that they will be mirror images of each other. The method will then be to invert the signal from differential pressure gauge 23, thereafter to cross-correlate it with the signal is from gauge 18, in cross-correlator 26. Since the time-dependent variation in the differential pressure signals will substantially be due to local variations in the liquid fraction, one will be able, by cross-correlating these signals, to find the velocity of the liquid in an alternative manner in relation to the first embodiment of the invention. In order to calculate all fractions and rates, the further part of the method will be identical to that which has been described in the first embodiment of the invention hereabove. This second embodiment of the invention can be used as a complete three-phase flow rate meter, and one can, referring again to FIG. 1, remove the small electrodes 7a and 7b with appurtenant electronic circuits 9a and 9b, to simplify the device and to shorten sensor body 1. However, if it is used together with the first embodiment of the invention, one may achieve the advantage of redundancy in the measurement of the liquid velocity.

Figure 4:
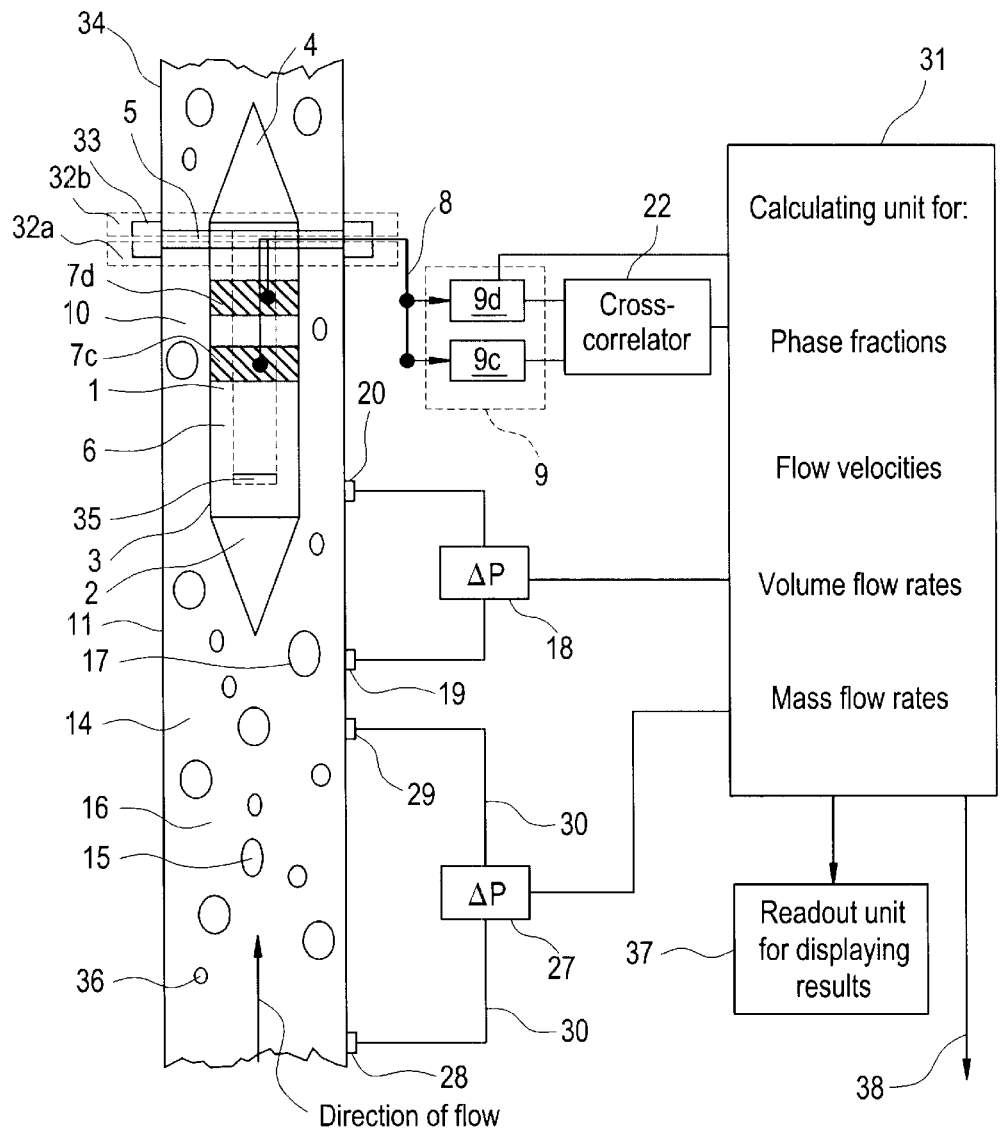
FIG. 4 shows a third embodiment of the invention with the transport pipe, the sensor body including electrodes, a differential pressure gauge in the upstream end of the sensor body, as well as an additional differential pressure gauge further upstream in relation to the sensor body.

In a third embodiment of the invention, referring to FIG. 4, a third differential pressure gauge 27 will be used, in a distance that is somewhat further upstream from sensor body 1, in a section of pipe 11 that is without any intrusive parts or other disturbances. In addition, it is presumed that this part of the pipe is mounted approximately vertically, so that the two terminals 28 and 29 for the differential pressure gauge 27 are mounted with a certain minimum vertical distance, h. therebetween. The differential pressure gauge 27 and appurtenant terminals 28 and 29 can for that matter also be placed downstream from sensor body 1. By means of this device, a differential pressure can be measured that is dependent on the mass density of the multiphase mixture 14, through the static pressure difference arising due to the weight of the mixture. Since the mass density of mixture 14 is a function of the mass densities of the individual phases, as well as the three phase fractions given in Equation 9, one can, by combining this with the measurement of the electrical characteristics, and the relation in Equation 2 and Equation 3, between one of the electrodes, e.g. 7d with appurtenant detector circuit 9d, and pipe wall 11, calculate the three phase fractions. The relation between the gas fraction $\phi_{gas}$, and the static pressure difference, $\Delta P$, is as stated in Equation 10 below:

$$\phi_{gas} = \frac{(\rho_{liq} - \rho_{liq})gh + \Delta P + Fr}{(\rho_{liq} - \rho_{gas})gh}, \quad \text{Equation 10.}$$

where, as previously stated, $$\rho_{liq} = \frac{\phi_{wat}}{\phi_{wat} + \phi_{oil}} \cdot \rho_{wat} + \frac{\phi_{oil}}{\phi_{wat} + \phi_{oil}} \cdot \rho_{oil}.$$

Here g is the acceleration of gravity, Fr is the friction loss and $\rho_{tpt}$ is the mass density of the fluid in the supply lines 30 to the differential pressure gauge 27, where the two last mentioned parameters must be known. Since $\phi_{gas}$ is given explicitly in Equation 10, one may find the other two phase fractions by means of Equation 2 and Equation 3, and thereafter the mass density of the mixture can be calculated by using Equation 9. In this case, one will use the first differential pressure gauge 18 for determining the liquid flow rate using the momentum equation (Equation 6), so that in this embodiment, and referring to FIG. 3, the differential pressure gauge 23 can be made redundant. In addition, one can, referring to FIG. 1, in a similar manner as in the second embodiment described hereabove, remove the small electrodes 7a and 7b with appurtenant detectors 9a and 9b and cross-correlator 21, to make the device simpler.

In all of the three above mentioned embodiments of the device, cross-correlation of the electrical signals from detectors 9c and 9d belonging to electrode pair 7c and 7d, will be used for a determination of the gas velocity, which velocity in most cases is presumed to be different from the velocity of the liquid.

Figure 5:
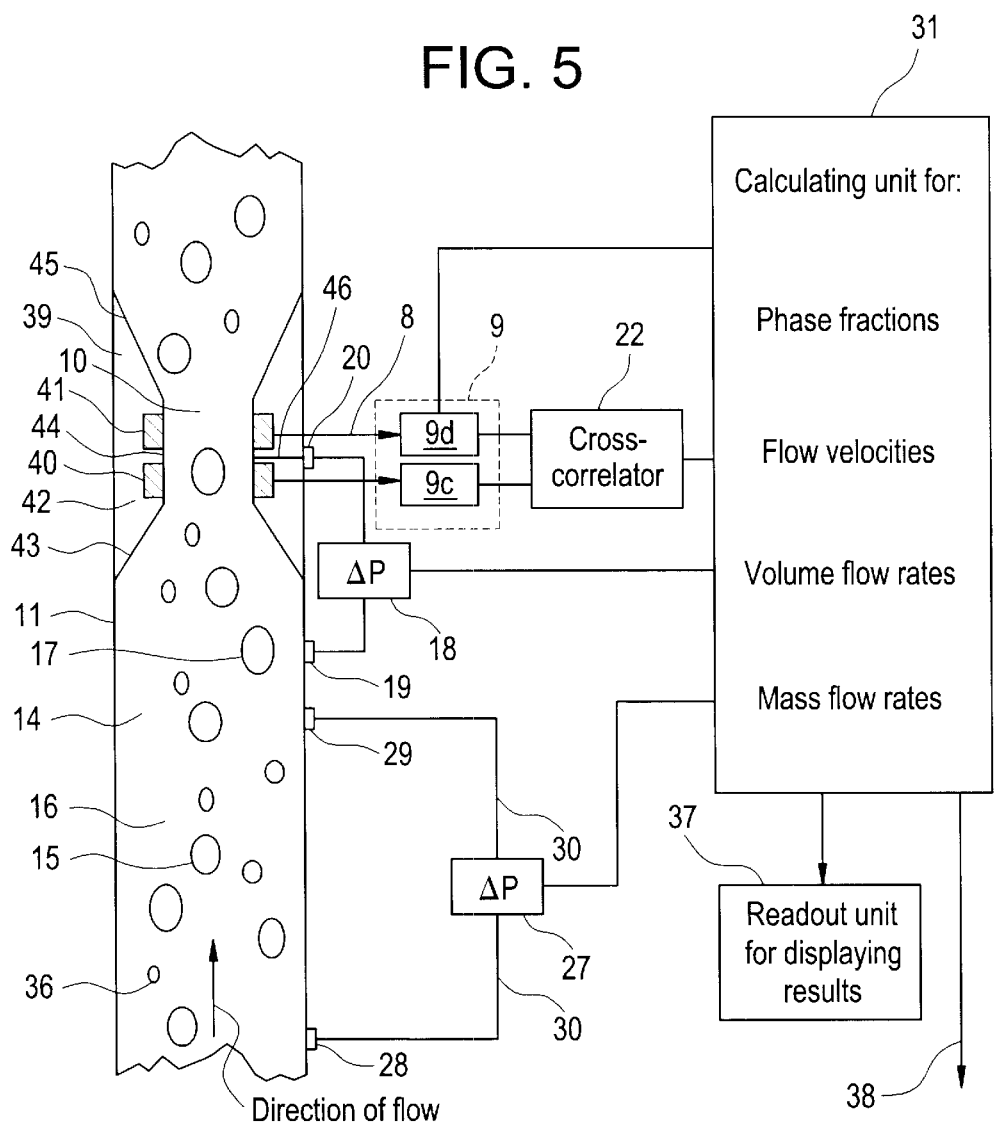
FIG. 5 shows a fourth embodiment of the invention with the transport pipe, a sensor insert having inside electrode devices, a differential pressure gauge in the upstream end of the sensor body, as well as an additional differential pressure gauge further upstream in relation to the sensor body.
Figure 6A:
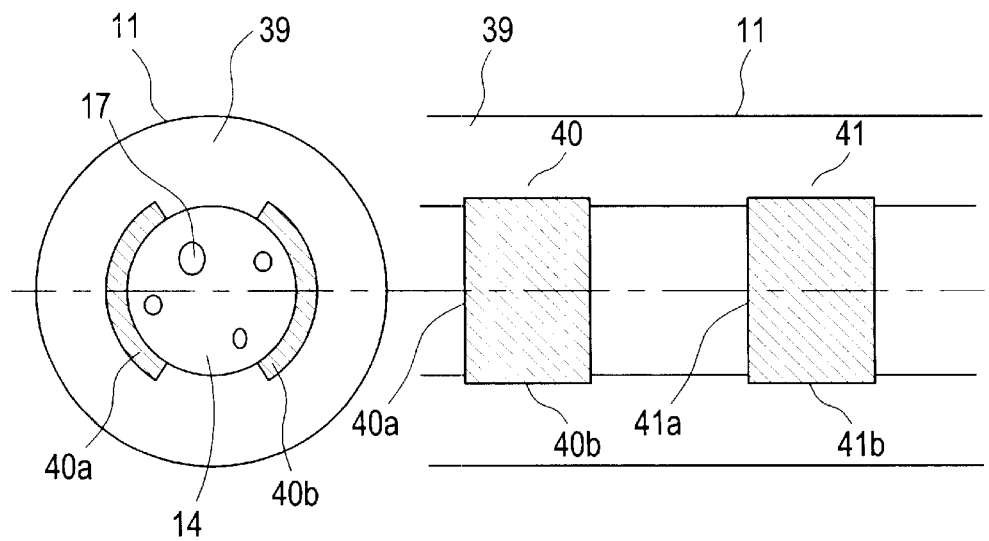
FIG. 6 shows two possible configurations of the electrode devices mounted in the cylindrical part of the sensor insert.
Figure 6B:
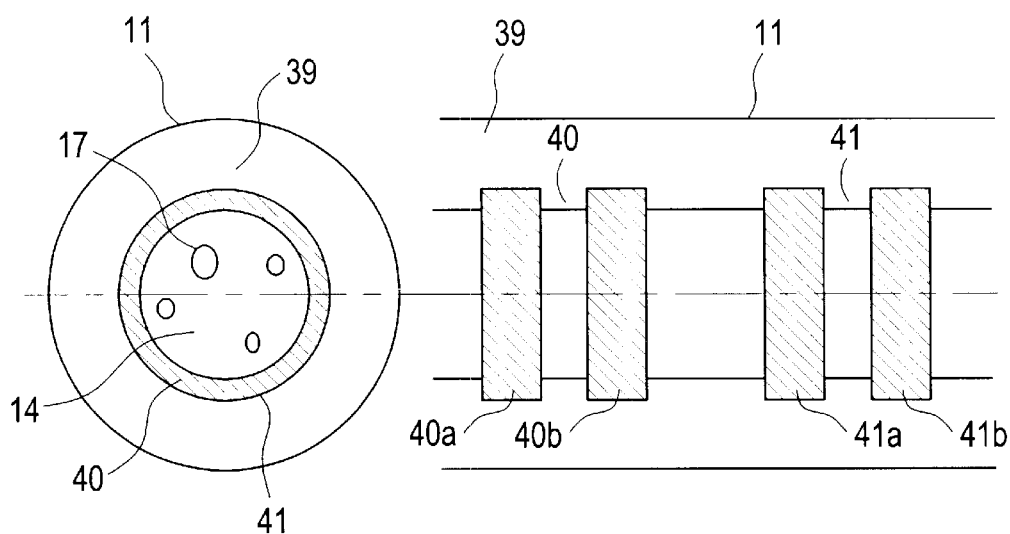

In a fourth embodiment of the invention, and referring to FIG. 5, the same first differential pressure gauge 18 will be used to measure the pressure difference between a terminal 19 upstream from a sensor insert 39 and a terminal 20 in the narrowing provided by the sensor insert 39. In the same manner as previously described, this differential pressure could equally well be measured between a position downstream from sensor insert 39 and a position in the narrowing of sensor insert 39. In this embodiment, sensor insert 39 and hence the narrowing including the measuring area 10, is configured in an alternative manner relative to the previous embodiments. Sensor insert 39 is made from an electrically insulating material 42, that e.g. may be a thermoplastic or some other electrically insulating material. It is manufactured starting from a solid bolt having an outer diameter that corresponds to the inner diameter of pipe 11. Then, a converging section 43 has been machined out, and from there a cylindrical section 44 than constitutes measuring area 10, before machining out a diverging section 45 via which one returns to the original inner diameter of pipe 11. In the measuring area 10 there is placed two electrode devices 40 and 41 for measuring the electrical characteristics of the flowing medium 14. In this case, it is not possible to utilize the wall of pipe 11 as a counter electrode, and therefore, pairs of electrodes must be built in to carry out the measurement. Examples of the these electrode pairs are shown in FIGS. 6a and 6b, and it is therefore referred to these figures for a more detailed description of how to arrange such devices. In FIG. 6a appear two curved electrodes 40a and 40b placed opposite each other across the cross section of pipe 11. These electrodes are duplicated further downstream, in the form of electrodes 41a and 41b, in the cylindrical section 44 of sensor insert 39. Alternatively, as shown in FIG. 6b, they can be formed as rings located close to each other, e.g. as shown with electrodes 40a and 40b, where this ring pair is duplicated again downstream in the form of electrodes 41a and 41b. One of these devices, e.g. 40, is applied for measuring the electrical characteristics of the flowing medium 14, for use when calculating the fractions. Thereafter, the signals from 40 as well as 41 are used for cross-correlation, in order to find the velocity of the large disturbances 17, that will often be the gas. Corresponding to the other embodiments of the invention, and referring to FIG. 5, the devices 40 and 41 will be connected to electronic circuits 9c and 9d by means of wires 8, for generating signals to be processed by cross-correlator 22, prior to transmitting the result thereof to the calculating unit 31. One of the pressure taps, represented by terminal 20, to differential pressure gauge 18, will be placed in the cylindrical part 44 of the narrowing. Therefore, there must be a channel 46 through sensor insert 39 that reaches measurement area 10 to be able to detect a correct differential pressure. Further, the same third differential pressure gauge 27 will be used at a distance a little further upstream, or for that part downstream, from sensor insert 39, in an area of pipe 11 without any intrusive parts or other disturbances. Also in this case it is presumed that this part of the pipe has been mounted vertically, so that the two terminals 28 and 29 for differential pressure gauge 27 are mounted with a certain minimum vertical distance, h, between them. In order to carry out the calculations, one proceeds in the same manner as in the third embodiment, however one utilizes the measurement of the electrical characteristics from e.g. 40, inserted in equation 3, this equation is combined with equation 2, and equation 10 receiving its value from differential pressure gauge 27. Further, the mass density of the mixture is calculated by using equation 9, and the first differential pressure gauge 18 is applied for determining the liquid flow rate using equation 6. The velocity of the gas is calculated using equation 4, receiving its input data from the electronic circuits 9c and 9d connected to devices 40 and 41.

All calculations are made in a calculating unit 31 in the form of a computer that also includes an input stage for reading and converting data from measuring units 9, 18, 22 and 27. The data are then processed by a data processor controlled by software suitable therefor. Calculating tools can be input as part of the software, for recalculating the results from the prevailing pressure and temperature conditions during measurement, to standard pressure and temperature conditions. The calculating unit 31 also includes a means for storing data. Further, the calculating unit 31 comprises an output stage where the results of the calculations can be transmitted to a readout unit 37 for displaying data on e.g. a screen, the results can be sent to a printer unit, or the results can be sent via a communication line 38 to e.g. the user's control system.

What is claimed is:

1. A method for determining cross-section fractions, as a basis for flow rate determination, for individual phases in a flow of a multiphase mixture at a location in a pipe, velocities of gas and liquid phases respectively in the flow being determined by cross-correlating measurements of one of parameters permittivity and conductivity of the mixture, executed at a specific position at said relevant location and upstream or downstream thereof, the measurements of said one parameter also providing direct information related to the cross-section phase fractions, and a narrowed flow passage being provided for measuring differential pressure between a first position upstream or downstream of said narrowed passage and a second position at said passage, said passage having a known cross-section area, comprising the steps of:

arranging said narrowed passage so as to extend some distance along the pipe to each side of said specific position, measuring said one parameter by means of electrodes arranged in said narrowed flow passage, and calculating the final cross-section fractions for the phases from the differential pressure, from values known beforehand regarding the mass densities of the phases, from the respective gas and liquid phase velocities, from said one parameter and from said cross-section area.

2. The method of claim 1, wherein the measurements of said one parameter are made using relatively wide electrodes for determining the velocity of one phase by cross-correlation, and simultaneously using relatively narrow electrodes for determining the velocity of the other phase or both phases by cross-correlation.

3. The method of claim 1, wherein differential pressure is measured between said first and second positions by means of lead-throughs/pressure taps, through a pipe wall at, and upstream or downstream of, a sensor body placed substantially on a pipe axis to provide said narrowed flow passage between the pipe wall and the sensor body, said sensor body at the same time comprising pairs of wide and narrow electrodes for measuring said one parameter, counter electrodes being constituted by said pipe wall or a separate tubular counter electrode device arranged close to the inside of said pipe wall, however insulated electrically therefrom.

4. The method of claim 1, wherein the cross-section fractions that have been determined, are combined with the already determined velocities of the phases, as well as the cross-section area of the narrowed passage, in order to determine the volume flow rates of the individual phases at the current conditions at the location.

5. The method of claim 4, wherein the combination process is adjusted using a suitable calculating tool for determining volume flow rates at standard pressure and temperature conditions.

6. The method of claim 4, wherein the volume flow rates that have been determined, are combined with the mass densities known beforehand regarding the individual phases, in order to determine the mass flow rates of the individual phases under the current conditions at the location.

7. The method of claim 6, wherein the combination process is adjusted using a suitable calculation tool for determining mass flow rates at standard pressure and temperature conditions.

8. The method of claim 1, wherein a further differential pressure is measured between a third position at the narrowed flow passage and a fourth position downstream or upstream of said passage, whereby the velocity of one of said phases is determined additionally by cross-correlating the two differential pressure measurements.

9. The method of claim 1, wherein said differential pressure is measured by means of lead-throughs/pressure taps through a pipe wall, upstream or downstream of, and at a sensor insert that consists of a converging passage continuing in said narrowed flow passage and ending in a diverging passage, and that the measurement of said one parameter is made by means of electrodes arranged on the inside of said narrowed flow passage in said sensor insert.

10. A system for determining cross-section fractions, as a basis for flow rate determination, for individual phases in a flow of a multiphase mixture at a location in a pipe, velocities of gas and liquid phases respectively in the flow being determined by cross-correlating measurements of one of parameters permittivity and conductivity of the mixture, carried out at a specific position at said relevant location and upstream or downstream thereof the measurements of said one parameter also providing direct information related to the cross-section phase fractions, said system comprising a narrowed flow passage in the pipe with means for measuring differential pressure between a first position upstream or downstream of said narrowed passage and a second position at said passage, said passage having a known cross-section area, whereby said narrowed passage being arranged so as to extend some distance along the pipe to each side of said specific position, electrodes arranged in said narrowed flow passage for measuring said one parameter, and means for calculating, from said differential pressure, from values known beforehand regarding the mass densities of the phases, from respective gas and liquid phase velocities, from said one parameter, and from said cross-section area, the final cross-section fractions of the phases.

11. The system of claim 10, wherein said electrodes for measuring said one parameter comprise relatively wide electrodes for determining the velocity of one phase by means of cross-correlation, and relatively narrow electrodes for determining the velocity of the other phase or both phases by means of cross-correlation.

12. The system of claim 10, further comprising:

a sensor body placed substantially on a pipe axis to provide said narrowed flow passage between the pipe wall and the sensor body, said sensor body at the same time comprising pairs of wide and narrow electrodes for measuring said one parameter counter electrodes being constituted by the pipe wall or a separate tubular counter electrode device arranged close to the inside of a pipe wall, however electrically insulated thereof, and lead-throughs/pressure taps through the pipe wall at said first and second positions, for measuring differential pressure between these two positions.

13. The system of claim 10, wherein said means for calculating said final cross-section fractions are further operative to combine the cross-section fractions determined, with the already determined velocities of the phases, as well as the cross-section area of said narrowed passage, in order to determine the volume flow rates of the individual phases under the current conditions at the location.

14. The system of claim 13, including a calculating tool for adjusting the combination process so as to determine volume flow rates at standard pressure and temperature conditions.

15. The system of claim 13, wherein said means for calculating said final cross-section fractions are further operative to combine the volume flow rates determined, with the mass densities known beforehand regarding the individual phases, to determine the mass flow rates of the individual phases under current conditions at the location.

16. The system of claim 15, including a calculating tool for adjusting the combination process so as to determine mass flow rates at standard pressure and temperature conditions.

17. The system of claim 10, including further means for measuring differential pressure between a third position at said narrowed flow passage and a fourth position downstream or upstream of said passage, whereby the velocity of one of said phases can be determined additionally by cross-correlating the two differential pressure measurements.

18. The system of claim 10, further comprising:

a sensor insert consisting of a converging passage continuing in said narrowed flow passage and ending in a diverging passage, said sensor insert having electrodes arranged on the inside of said narrowed passage for measuring said one parameter, and lead-through/pressure taps through a pipe wall, upstream or downstream of and at said sensor insert, for measuring said differential pressure.

* * * * *